United States Patent [19]

Ohnishi

[11] Patent Number: 4,681,899
[45] Date of Patent: Jul. 21, 1987

[54] METHOD OF PREVENTING THE GROWTH OF MALARIA PARASITES IN ERYTHROCYTES

[76] Inventor: S. Tsuyoshi Ohnishi, 4220 Pine St., Philadelphia, Pa. 19104

[21] Appl. No.: 717,978

[22] Filed: Mar. 29, 1985

[51] Int. Cl.4 .................... A61K 31/18; A61K 31/135
[52] U.S. Cl. .................................. 514/602; 514/652; 514/895
[58] Field of Search ........................ 514/895, 602, 652

[56] References Cited

U.S. PATENT DOCUMENTS 4,428,883  1/1984  Hussain ............................... 514/652
4,556,678  12/1985  Hsiao ................................... 514/652

FOREIGN PATENT DOCUMENTS 56-68610  6/1981  Japan .................................... 514/602

Primary Examiner—Allen J. Robinson
Attorney, Agent, or Firm—Caesar, Rivise, Bernstein, Cohen & Pokotilow, Ltd.

[57] ABSTRACT

A method of inhibiting the growth of malaria parasites in red blood cells not by affecting the parasites themselves but by affecting the metabolism of red blood cells. The method involves introducing and maintaining beta-adrenergic blockers or calmodulin antagonists in the blood stream at a concentration enough to suppress the parasite growth.

5 Claims, 4 Drawing Figures

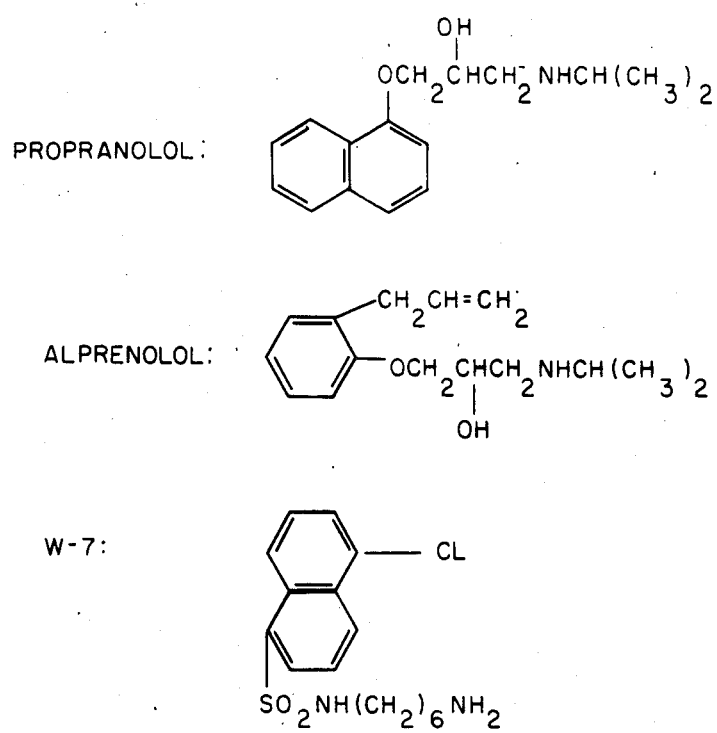
FIG. 1. STRUCTURE OF DRUGS
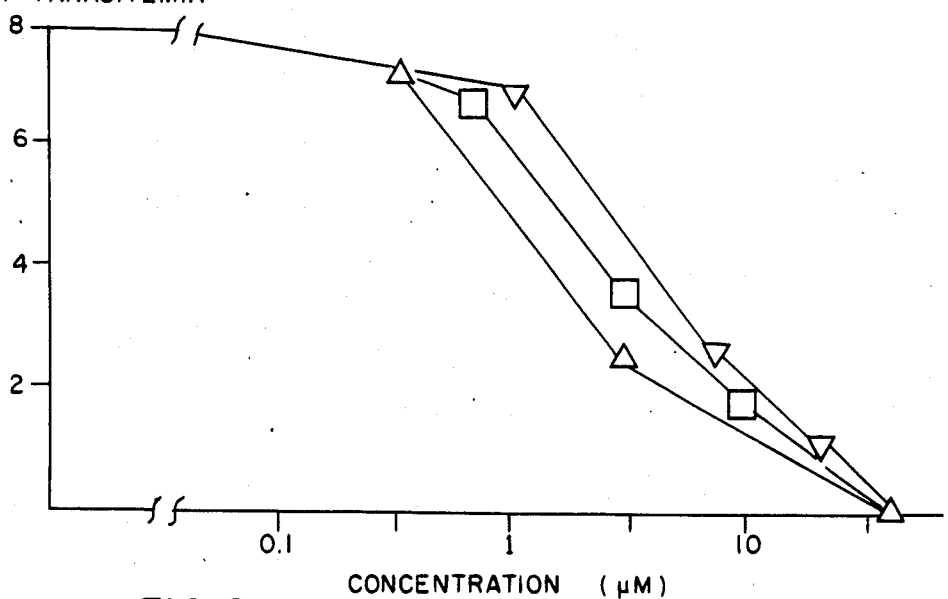
FIG. 2. INHIBITION OF THE GROWTH OF P. FALACIPRUM IN THE CULTURE BY VARIOUS DRUGS.
△ PROPRANOLOL    □ ALPRENOLOL    ▽ W-7

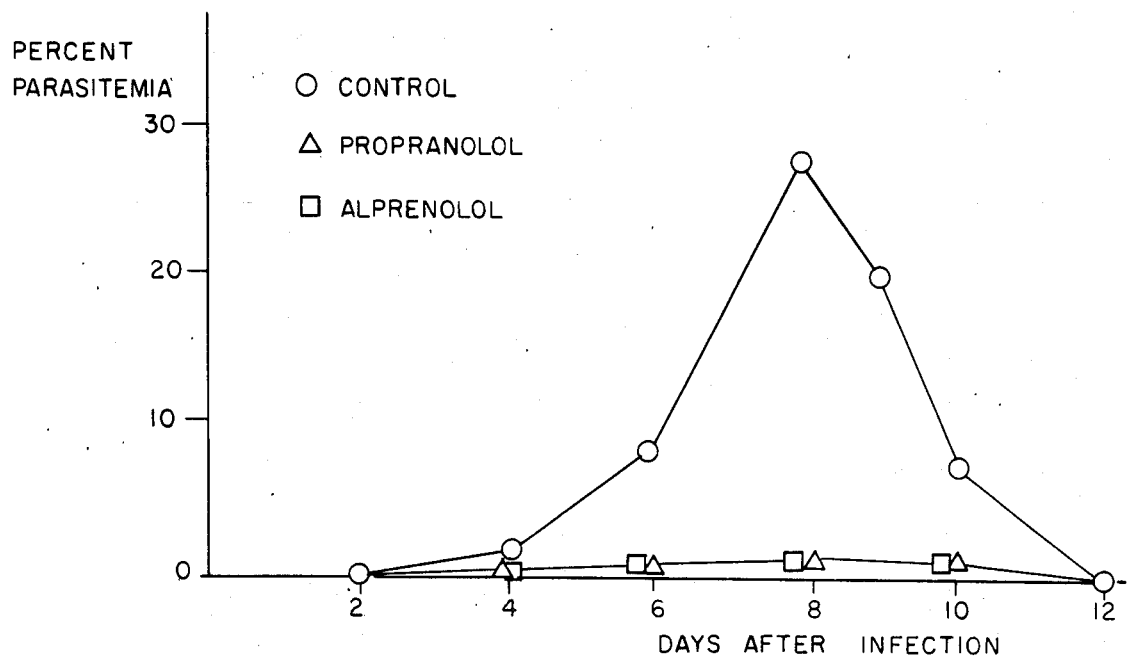
FIG. 3. EFFECT OF ORAL ADMINISTRATION (3 MG./KG./DAY) OF PROPRANOLOL AND ALPRENOLOL ON THE GROWTH OF PARASITES OF P. FALACIPRUM IN MICE.
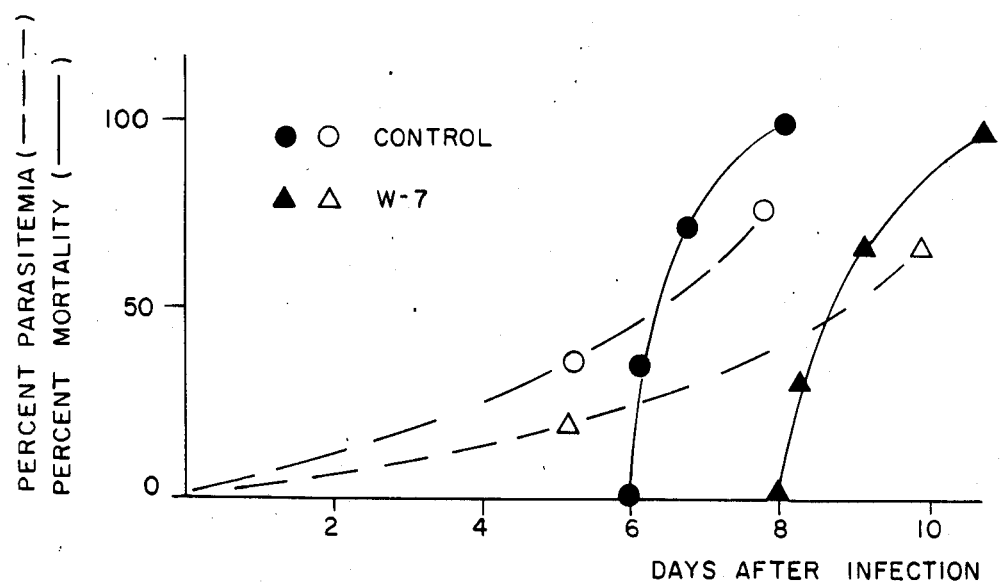
FIG. 4. EFFECT OF ORAL ADMINISTRATION (3 MG./KG./DAY) OF W-7 ON THE PARASITE GROWTH (DASHED LINE) AND THE MORTALITY (SOLID LINE) OF THE MICE INFECTED BY P. VINCKIEY.

METHOD OF PREVENTING THE GROWTH OF MALARIA PARASITES IN ERYTHROCYTES

BACKGROUND OF THE INVENTION

This invention relates to a chemotherapeutic method of inhibiting the growth of malaria parasites inside red blood cells. More precisely, this relates to a discovery of several drugs which could inhibit the growth not by affecting parasites but by affecting the red blood cells.

Significance

Malaria is one of the most important health problem in underdeveloped, tropical countries. It is estimated that more than a billion people in the world inhabit areas in which malaria is transmitted. Although chloroquine has been used as an effective drug, this drug seems to have some side effects. But of more importance, we know that malarial parasites are acquiring resistance to chloroquine. Recently a new drug mefloquine was introduced, but already resistant strains have appeared.

Another method to reduce malaria infection is to use insecticides to wipeout mosquitoes. However, insecticides may have toxicologic effects to the inhabitants as well as to the environment. It is also known that mosquitoes can acquire resistance to insecticides. Thus, campaigns against malaria have been deadlocked.

A difficulty in developing an effective chemotherapeutic treatment is to overcome the resistance-acquiring capability of malaria parasites. We have approached this problem from a unique angle. It is well known that people with homozygous sickle-cell and sickle-cell trait are relatively resistant to malaria infection. Malarial parasites do not grow well in sickle or trait red cells (Friedman, Proc. Natl. Acad. Sci. 75:1994(1978); Friedman et al. J. Trop. Med. Hyg. 28:777(1979)). It appears that no parasites have acquired the capability to grow normally in both sickle and trait red cells. The secret may be that these cells can inhibit the growth of parasites based upon altered physical properties of the red cells.

The present invention involves a method to suppress parasite growth by modifying the host's red cells. Since this method does not directly influence the metabolic activity of parasites, this method is essentially free from the strain-resistance problem.

The invention is expected to improve the quality of lives of over a billion people who live in malaria infested areas and could save lives of numerous malaria victims. Millions of travellers who visit tropical countries every year may also be able to use this as a prophylactic means.

Methods and Experimental Design (i) Drugs:

The compound W-7 was purchased from the manufacturer (Rikaken Co., Aichi Prefecture, Japan). Propranolol (both d- and l- form optical isomers) and alprenolol (both d- and l- form optical isomers) were the gifts of Ayerst Co. (Montreal, Canada) and A. B. Hassle Co. (Molndal, Sweden), respectively. Structures of these compounds are shown in FIG. 1.

The acute $LD_{50}$ of l-propranolol, l-alprenolol and W-7 in mice (oral administration) are 40, 278 and 75 mg/kg.

The usual effective dose of l-, d-propranolol (mixture of l-form, which is an active beta-adrenergic blocker, and d- form, which is an inactive beta-adrenergic blocker) in man as an anti-hypertensive drug is 160–480 mg daily in adults (3–8 mg/kg body weight/day).

(ii) Mice and Parasites:

Mice: Four to eight-week-old BALB/C male and female mice from a breeding colony were used.

Parasite: Stabilates of p. Vinchei TCC 30091) and p. Falciparum (FCR-3 knobless) were used.

(iii) Measurement of Parasitemia:

In vitro method: A small aliquot of sample was taken from the culture from which a smear was made.

In vivo method: The tail vein was nicked and a blood droplet was smeared.

The smears were stained with Giemsa, infected erythrocytes (which contain trophozoite and schizont stage parasites) were counted and percent parasitemia estimated.

(iv) In vitro Experiments:

p. Falciparum was grown by continuous culture with human erythrocytes (Type A blood from blood bank) incubated in culture medium consisting of RPMI medium with human serum (under the method of Trager and Jenson (Science 193:673(1976)). The cultures were maintained in 17 mm microtiter wells; we started the culture at 0.2% parasitemia (hematocrit 5%) and asynchronously growing cultures were harvested at 48 hours (15-20% of parasitemia). A control and seven different drug concentrations (0.1, 0.3, 1, 3, 10, 30, 100 uM) were tested in triplicates. Drugs were aseptically prepared, and added to the the microtiter wells in which parasitized red blood cells were cultured.

At 48 hours, percent parasitemia was determined, from which the dose-response relationship was determined.

(v) In vivo Experiments:

Approximately $10^5$ p. Vinchei parasites were injected intraperitoneally (I.P.) into a donor mouse and at the time of ascending parasitemia, the infected mouse was exsanguinated and red blood cells are prepared for in vivo experimentation.

A control and a drug concentration (approximately 3 mg/kg body weight/day) were provided orally via drinking water. Water containing drugs were prepared daily. Water intake were monitored daily to insure proper dosage and hydration levels. A commercial food pellet were provided ad libitum.

To each mouse, $10^6$ parasitized red blood cells were injected I.P., and daily blood samples were collected from the tail vein to monitor the levels of parasitemia.

Five mice were used for each group tested.

During the experimentation, we monitored both the percent parasitemia and percent survival rate of each experimental group.

Results

Through studies on sickle red cells (Ohnishi, Blood Cells 8:337(1982); Ohnishi et al. Canad. J. Physiol. Pharmacol. 60:148(1982); Ohnishi, in a book entitled "Calmodulin: Antagonists and Cell Function" edited by H. Hidaka and D. J. Hartshorne (in press by Academic Press)), Ohnishi found that beta-adrenergic blockers, such as propranolol and alprenolol as well as calmodulin antagonists such as W-7 altered the red cell metabolism and thus affected the cell sickling. From these data, he speculated that these drugs would also affect the growth of malaria parasites. In deed that was the case.

As shown in FIG. 2, at the concentration range below 10 uM these agents effectively inhibited the growth of *Plasmodium falciparum* in in vitro culture. The most significant observation is that both d- and l- form isomers of beta-adrenergic blockers demonstrated the same inhibitory effect. It is well known that d- form of beta-adrenergic blockers have a very weak blocking action (less than 1/100 of that of l- form). This observation suggests that the inhibition of parasite growth is not related to their beta-adrenergic blocking action. Since beta-adrenergic blockers reduce the contractility of the heart (for example, propranolol has been used as an anti-hypertension drug), it there is a limit in the daily dosage when they would be used as an anti-malaria drug. However, since d- form has a very weak blocking action, this form is expected to have more effective anti-malaria activity.

Ohnishi tested an in vivo efficacy of these drugs using mice infected by *p. Falciparum*. As shown in FIG. 3, both l- and d- form of propranolol (administered 3 mg/kg/day orally) effectively inhibited the growth of parasites in mice. At this dosage, no side effect was observed in mice.

Using *p. Vinckei* and a mice model, Ohnishi has also tested the efficacy of W-7. As shown in FIG. 4, oral administration of W-7 (3 mg/kg body weight) suppressed the growth of parasites, and consequently extended their life span after infection.

I claim:

1. A method of inhibiting the growth of malaria parasites in a malaria victim comprising administering to said victim in a concentration sufficient enough to inhibit the growth of malaria parasites of a material selected from the group consisting of l-propranolol; l-, d-propranolol, l-alprenolol and N-(6-aminohexyl)-5-chloro-1-naphthalenesulfonamide.

2. The method of claim 1 wherein said material is administered orally at a dosage of 3 mg/kg/day.

3. The method of claim 1 wherein said material is administered orally at a dosage of 6 mg/kg/day.

4. The method of claim 1 wherein said material is administered intravenously at a dosage of 1 mg/kg/day.

5. The method of claim 2 wherein the material is N-(6-aminohexyl)-5-chloro-1-naphthalenesulfonamide.

* * * * *